United States Patent
Benech et al.

[11] Patent Number: 5,978,073
[45] Date of Patent: Nov. 2, 1999

[54] OPTICAL DEVICE FOR DETECTING THE CHARACTERISTICS OF MOVING PARTICLES

[75] Inventors: Pierre Benech; Alain Cartelier, both of Grenoble; Isabelle Schanen, La Tronche, all of France

[73] Assignee: Schneider Electric SA, France

[21] Appl. No.: 09/091,180

[22] PCT Filed: Jan. 11, 1996

[86] PCT No.: PCT/FR96/00048

§ 371 Date: Jun. 10, 1998

§ 102(e) Date: Jun. 10, 1998

[87] PCT Pub. No.: WO97/25607

PCT Pub. Date: Jul. 17, 1997

[51] Int. Cl.[6] .............. G01P 3/36; G01B 9/02; G01N 15/02; G01N 21/00

[52] U.S. Cl. ............ 356/28.5; 356/28; 356/349; 356/336; 356/338

[58] Field of Search ............ 356/28.5, 28, 349, 356/336, 338

[56] References Cited

U.S. PATENT DOCUMENTS

| | | | |
|---|---|---|---|
| 4,540,283 | 9/1985 | Bachalo | 356/336 |
| 5,094,526 | 3/1992 | Freud et al. | 356/28.5 |
| 5,155,549 | 10/1992 | Dhadwal | 356/336 |
| 5,513,004 | 4/1996 | Naqwi et al. | 356/336 |
| 5,793,478 | 8/1998 | Rader et al. | 356/28 |

FOREIGN PATENT DOCUMENTS

| | | |
|---|---|---|
| 0184269 | 6/1986 | European Pat. Off. . |
| 0638797 | 2/1995 | European Pat. Off. . |
| 4240769 | 6/1994 | Germany . |
| 2213018 | 8/1989 | United Kingdom . |
| 84/04592 | 11/1984 | WIPO . |

*Primary Examiner*—Frank G. Font
*Assistant Examiner*—Roy M. Punnoose
*Attorney, Agent, or Firm*—Parkhurst & Wendel

[57] ABSTRACT

The device uses the principle of the Doppler effect laser velocimeter. It comprises emitter and receiver optic guides formed by integrated optics techniques on a single substrate, preferably made of glass. The emitter guides, connected to a light source, produce two mutually coherent beams inclined with respect to one another in such a way as to constitute interference fringes in a measuring volume situated outside the substrate. The receiver guides transmit the light diffused by the passage of particles in movement through the measuring volume to a detection and processing circuit. The substrate is mounted in a support fixed in an orifice of a wall along which a fluid flows transporting the particles to be examined. The substrate comprises a face which comes into contact with the fluid. This device enables the velocity, size and/or number of particles in movement in a fluid moving along a wall to be determined.

10 Claims, 8 Drawing Sheets

OPTICAL DEVICE FOR DETECTING THE CHARACTERISTICS OF MOVING PARTICLES

BACKGROUND OF THE INVENTION

The invention relates to an optic device for detection of characteristics of particles in movement in a fluid flowing along a wall, a device comprising a light source, means, connected to the light source, for producing at least two mutually coherent light beams forming between them a predetermined angle so as to form an interference zone constituting a measuring volume on the path of the fluid, optic means for detection of the light diffused by particles passing through the measuring volume, optoelectronic means for detection, connected to the optic means for detection and supplying electronic signals representative of the light diffused, and processing means, connected to the optoelectronic means for detection.

A Doppler effect laser velocimeter enables the velocity of submicronic particles in a fluid to be measured. A velocimeter of this kind is based on particles passing through a succession of equidistant dark and bright zones belonging to a network of interference fringes.

FIG. 1 illustrates the principle of Doppler effect laser velocity measurement using the fringes method. Two coherent light beams 1 and 2, originating from the same laser 3, cross at the focal point of a convergent lens 4 inside a measuring volume 5. FIG. 2 represents the measuring volume 5 in greater detail. Inside the measuring volume 5, a system of interference fringes appears disposed according to equidistant planes parallel to the internal bisecting line of the two beams 1 and 2. The distance between two successive planes is the interfringe distance i. A particle driven by a fluid in movement perpendicularly to the fringes (axis X'X of FIG. 2, arrow 6 of FIG. 1), crosses the measuring volume 5 and passes successively through in the dark and bright fringes. The light flux diffused by a particle is modulated at a frequency proportional to its velocity. The light diffused by a particle is collected by an optic detection device. The diffused light is generally measured by retro-diffusion, that is to say on the side where the emission source constituted by the laser 3 is located, as represented in FIG. 1. The detection device comprises an objective 7 with fairly wide opening to collect the light diffused by the particles and form the image of the measuring volume on a diaphragm situated in front of a photo-multiplier 8. The latter supplies electrical signals representative of the light diffused by the particles to an electronic processing circuit 9. The signals supplied to the processing circuit 9 are presented in the form of a succession of sine wave trains, as represented in FIG. 3. Each of the trains, one of which is represented between two broken lines, is due to the passage of a particle in the measuring volume 5. The frequency of a sine wave train is representative of the velocity of the corresponding particle in the measuring volume. The processing circuit performs a frequency analysis of the signals. Known processing techniques use spectral analysis, frequency followers or image correlation. These various techniques enable mean values of the velocity of a particle to be obtained. Counting techniques, for their part, enable instantaneous values of the velocity of a particle to be obtained.

The Doppler effect laser velocimeter has up to now remained reserved for laboratory measurements. Known velocimeters are costly and require difficult adjustments, notably adjustment of the angle A (FIG. 1) of the beams 1 and 2. Modification of the angle A in fact modifies the interfringe distance i, and consequently the frequency of the measured signals. The optic detection device also has to be carefully aligned.

The Doppler effect laser velocimeter has up to now been used more particularly for measuring the velocity of particles in a fluid or, indirectly, for friction measurement near a wall. With known velocimeters, a section of the wall has to be transparent. The light beams reach the wall with a low incidence and the signals collected are very noisy on account of the light reflections on the walls. Only long and delicate optic adjustments, impracticable in the industrial world, enable acceptable signal-to-noise ratios to be obtained, in a laboratory.

SUMMARY OF THE INVENTION

The object of the invention is to provide an optic device for detection of characteristics of particles in movement which is inexpensive and can be achieved industrially.

According to the invention, this object is achieved by the fact that the means for producing light beams comprise at least one pair of two emitter optic guides, the optic means for detection comprise at least one optic receiver guide comprising an input end having an axis passing through the centre of the measuring volume, said emitter and receiver guides being achieved on a single substrate by integrated optics techniques, the geometry of the emitter guides being such that the measuring volume is arranged outside the substrate at a preset distance from a face of the substrate, the substrate being mounted in a support designed to be fixed in an orifice of the wall in such a way that said face of the substrate is in contact with the fluid. In this way the device uses the principle of the Doppler effect laser velocimeter and comprises a fully integrated optic system designed to be implanted in a wall which may be opaque.

According to a development of the invention, the substrate comprises a flat guide between the emitter optic guides and said face of the substrate.

The beams produced by the emitter optic guides may be parallel beams obtained by an adiabatic transition formed at the end of the emitter guides, or convergent beams.

BRIEF DESCRIPTION OF THE DRAWINGS

Other advantages and features resulting therefrom will become more clearly apparent from the following description of different embodiments given as non-restrictive examples only and represented in the accompanying drawings in which.

DETAILED DESCRIPTION OF THE PREFERRED EMBODIMENT

Figure 4:
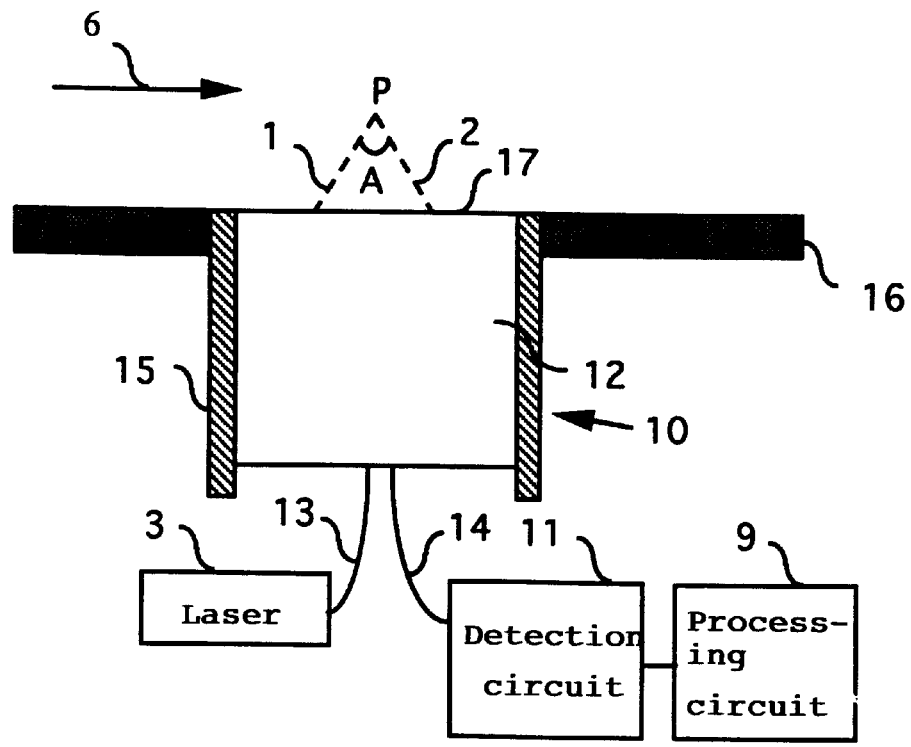
FIG. 4 represents, in schematic form, a device according to the invention comprising an optic head implanted in an opaque wall.

The device according to FIG. 4 comprises an optic head 10 connected to a laser 3 and to an optoelectronic detection circuit 11. The circuit 11 is connected to a processing circuit 9.

The optic head 10 is essentially constituted by a substrate 12 on which optic guides, or micro-guides, are formed by integrated optics techniques. Emitter optic guides are connected by an optic fibre 13 to an optic source constituted for example by a laser 3. They are designed in such a way as to supply two coherent optic beams 1 and 2 which converge at a measuring point P situated outside the substrate to form stable interference fringes at this point. The interfringe distance i is defined by the wave length of the laser and by the angle A of the beams 1 and 2. Receiver optical guides transmit signals representative of the light diffused by particles passing through the interference fringes to the detection circuit 11 via an optic fibre 14.

Particular embodiments of the optic guides will be described in greater detail with respect to FIGS. 5 to 9.

The substrate 12 is preferably a glass substrate on which the optic guides are achieved by ion exchange. As an example the substrate 12 can have a length of about 6 cm, and a width and thickness of about a few hundred micrometers, for example 0.5 mm.

The substrate is borne by a support 15 so as to form the compact and tight optical head 10 which can be implanted in a wall 16. The device thus enables particles in movement in a fluid flowing (arrow 6) along the wall 16 to be studied. The measuring volume, which is assimilated to a point P in the figure, is defined by the beams 1 and 2. The position of the point P with respect to the face 17 of the substrate 12 in contact with the fluid is determined with precision by the geometry of the optic guides implanted in the substrate. This position is defined by the angle A and by the distance separating the output points of the beams 1 and 2 from the substrate. The substrate is mounted in the support 15 in such a way that its face 17 is in contact with the fluid, preferably aligned with the internal face of the wall 16. The position of the measuring point P is thus defined with precision and it is possible to approach the wall 16 very closely, to less than around a hundred micrometers, while at the same time keeping a good signal quality.

Figure 5:
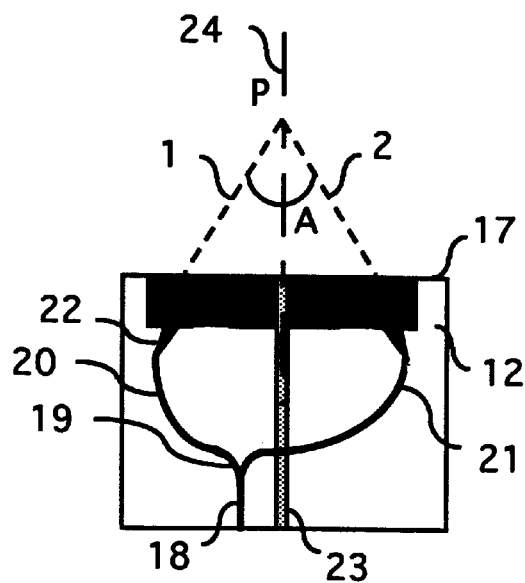
FIGS. 5 to 8 and 10 represent various particular embodiments of the optic head of FIG. 4.

FIG. 5 illustrates the arrangement of the guides on the substrate 12 according to a particular embodiment. A guide 18, the input emitter guide, is formed on the substrate. A beam splitter 19 formed by a Y junction divides it into a pair of two emitter guides 20 and 21. An adiabatic transition 22 is performed at the end of the guide 20 opening out onto the face 17. This adiabatic transition broadens the beam transmitted by the guide 20 so that the light beam 1 is a parallel beam. An adiabatic transition is also performed at the end of the guide 21 so as to form a parallel light beam 2.

The ends of the guides 20 and 21 are inclined with respect to one another in such a way that the beams 1 and 2 converge at a predetermined point P situated outside the substrate, forming a preset angle A between them.

In FIG. 5, a receiver guide 23 is formed on the substrate 12. It comprises a first, input end which gives out onto the face 17 of the substrate so that the axis 24 of this first end passes through the measuring point P. A second, output end of the guide 23 is designed to be connected to the detection circuit 11. The quantity of light diffused by a particle passing through the interference fringes at the point P is very small, for example about a few nanowatts for a one watt laser. It is therefore desirable that a maximum of light be received in the receiver guide 23 to facilitate subsequent processing of the signals.

In FIG. 5 the guide 23 is perpendicular to the face 17 of the substrate so as to optimize the quantity of light received. The width of the guide 23 is determined in such a way as to receive a maximum quantity of light while confining the portion of the measuring volume examined.

Figure 8:
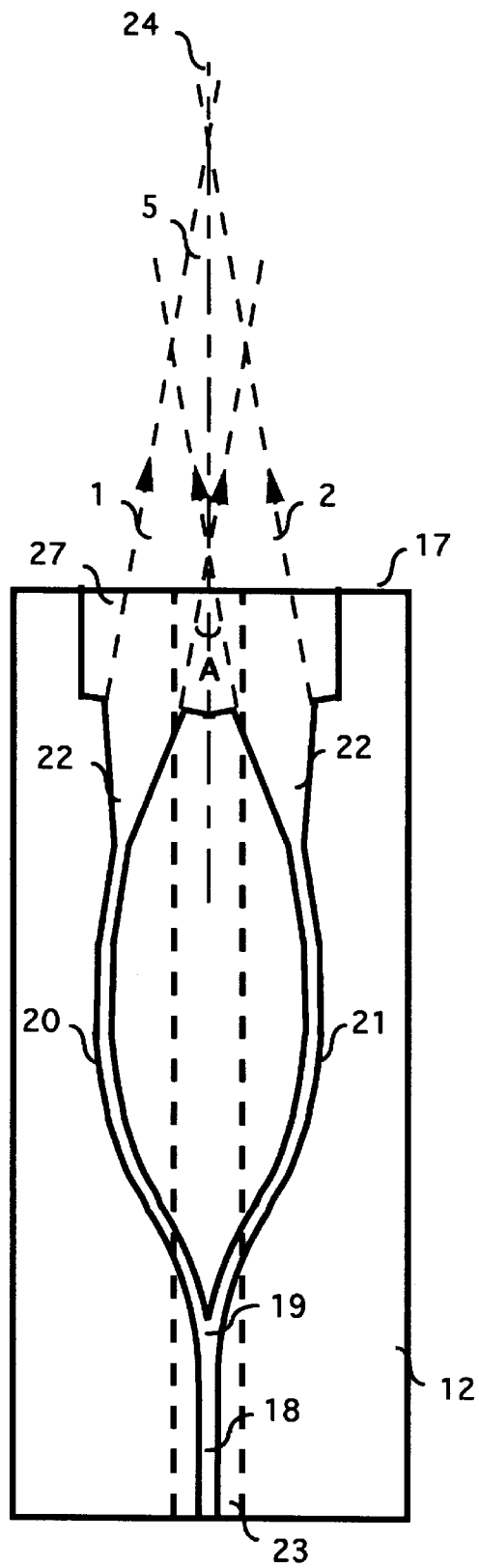

In FIG. 5 the guide 23 is straight. It can be formed in the same plane as the guides 20 and 21 or in a different plane (FIG. 8).

Figure 6:
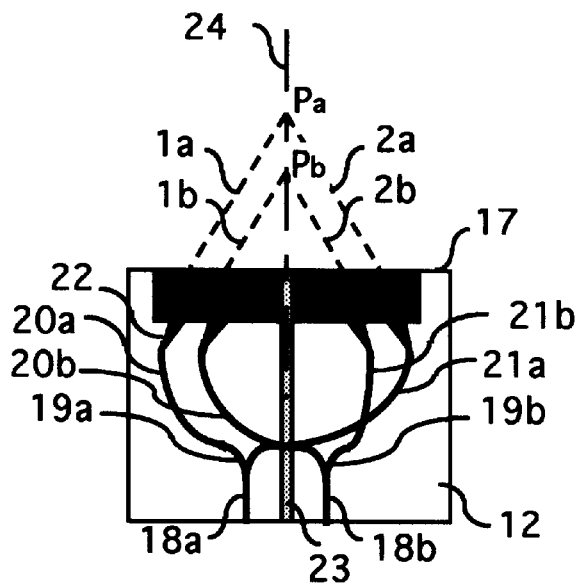

In FIG. 6 two pairs of emitter guides define two measuring points Pa and Pb aligned on the axis 24 of the input end of the receiver guide 23. Each of the measuring points is defined, as in FIG. 5, by an input emitter guide, respectively 18a and 18b, divided (junctions 19a and 19b) into a pair of emitter guides (20a and 21a; 20b and 21b) whose ends are enlarged, at 22, to form parallel beams (1a and 2a; 1b and 2b). There is a single receiver guide 23 enabling the two measuring points Pa and Pb to be observed. To be able to differentiate between the signals coming from the two measuring points, the latter are illuminated sequentially. The light signals applied respectively to the input emitter guides 18a and 18b are for example multiplexed. Multiplexing can be performed at the level of the optic source which then comprises two outputs respectively connected by two distinct optic fibres to the guides 18a and 18b and activated sequentially.

Figure 7:
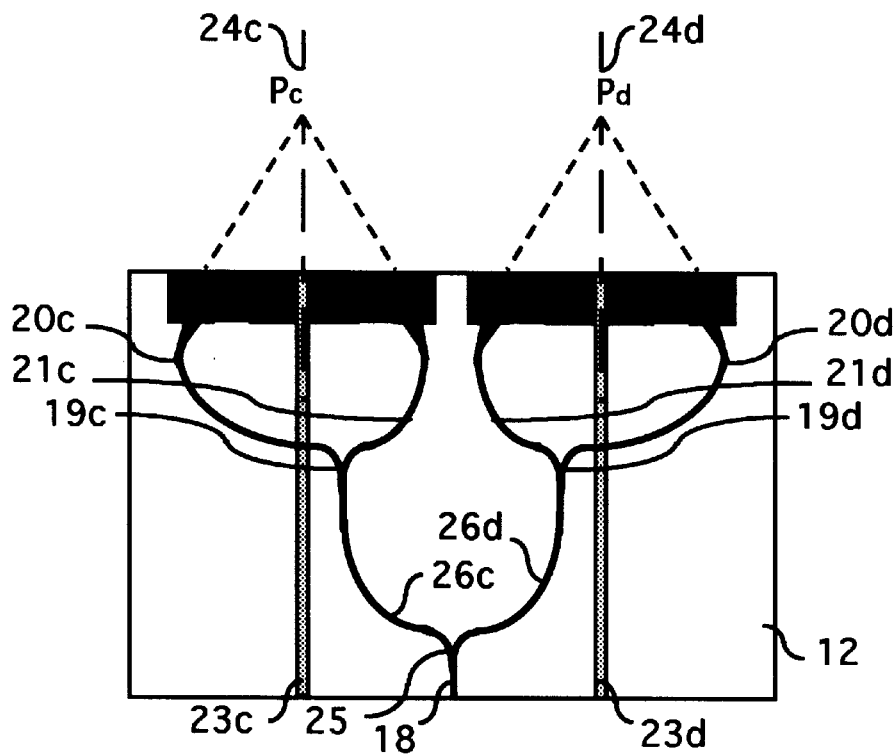

In FIG. 7, two pairs of emitter guides define two laterally offset measuring points, Pc and Pd. The pairs of emitter guides comprise a common input guide 18. A Y junction 25 divides the guide 18 into two intermediate guides 26c and 26d. Each intermediate guide is then divided by a corresponding Y junction 19c or 19d into a pair of emitter guides (20c and 21c or 20d and 21d) defining a measuring point (Pc or Pd). Two receiver guides 23c and 23d are disposed in such a way as to receive the light diffused respectively at the points Pc and Pd. The axis 24c of the input end of the receiver guide 23c passes through the point Pc and the axis 24d of the input end of the receiver guide 23d passes through the point Pd. In the figure, the signals coming from the points Pc and Pd are collected separately. If the receiver guides 23c and 23d are connected to the detection circuit 11 separately, electronic multiplexing can be performed at the level of the detection circuit 11.

According to an alternative embodiment which is not represented, emitter beam multiplexing can be performed in the optic head 10 itself. For this an optic modulator, or switch, is arranged on the path of each pair of emitter guides. Such a modulator is for example formed by a deposit of liquid crystals or by a thermo-optic process when the substrate 12 is a glass substrate.

Naturally it is possible to form more than two pairs of emitter guides on one and the same substrate 12 so as to define a plurality of measuring points arranged at preset locations with respect to the face 17 of the substrate.

FIG. 8 represents, on an enlarged scale, the parallel beams 1 and 2 which converge so as to define the measuring volume 5 in which the interference fringes form. In the particular embodiment of FIG. 8, the emitter guides are symmetrical with respect to the axis 24 of the receiver guide 23. The adiabatic transitions of the ends of the beams 20 and 21 form the parallel beams 1 and 2. A flat output guide 27 is formed at the output of the adiabatic transitions up to the face 17 so that the beams propagate freely in the substrate before interfering outside the substrate in the volume 5. The angle A is defined by the geometry of the ends of the guides 20, 21 and of their transitions 22.

Figure 9:
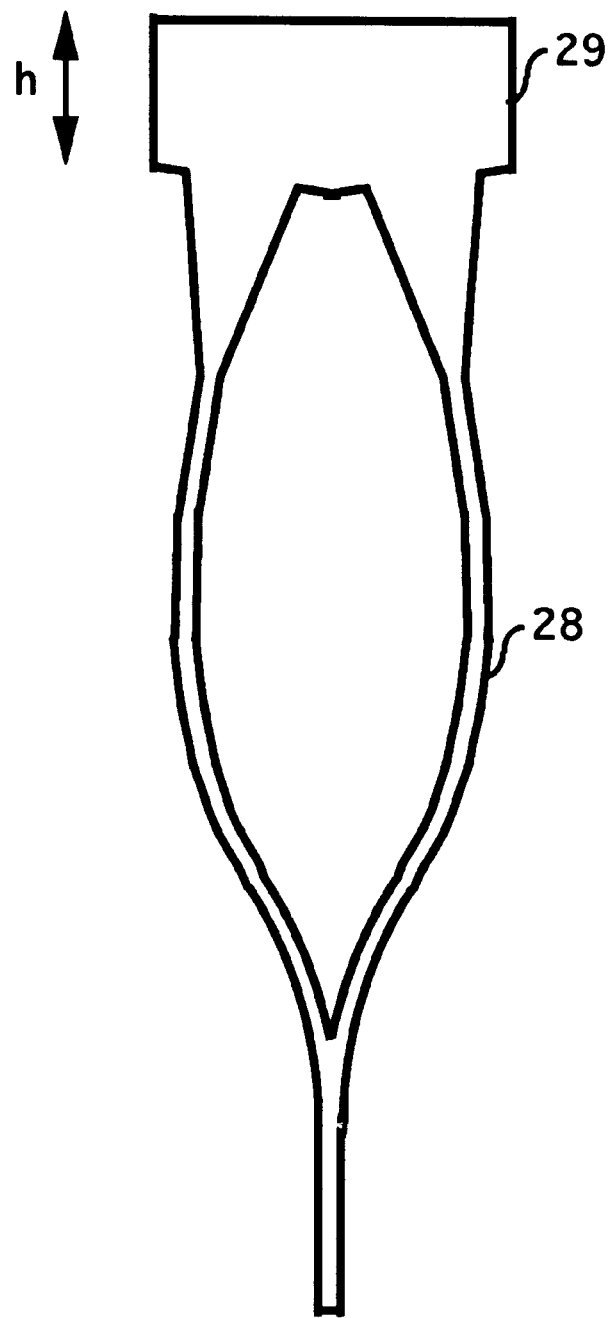
FIG. 9 illustrates a mask designed to fabricate an optic head according to FIG. 8.

A mask 28 represented in FIG. 9 enables the emitter guides of the optic head of FIG. 8 to be reproduced very precisely. The mask reproduces the geometry of the guides 18, 20 and 21 and of the adiabatic transitions 22 very exactly. It is terminated by a flat part designed to form the flat guide 27. This part has a height h such that interference of the beams 1 and 2 takes place outside the flat guide 27. When the optic head is fabricated, the mask is deposited on the substrate then removed after implantation of the ions. The substrate 12 is sawn and polished in the part forming the flat guide 27 so as to form the face 17 at a preset distance from the measuring volume 5. It is thus possible, from a single mask, to form optic heads defining measuring points at different distances from the face 17.

Figure 10:
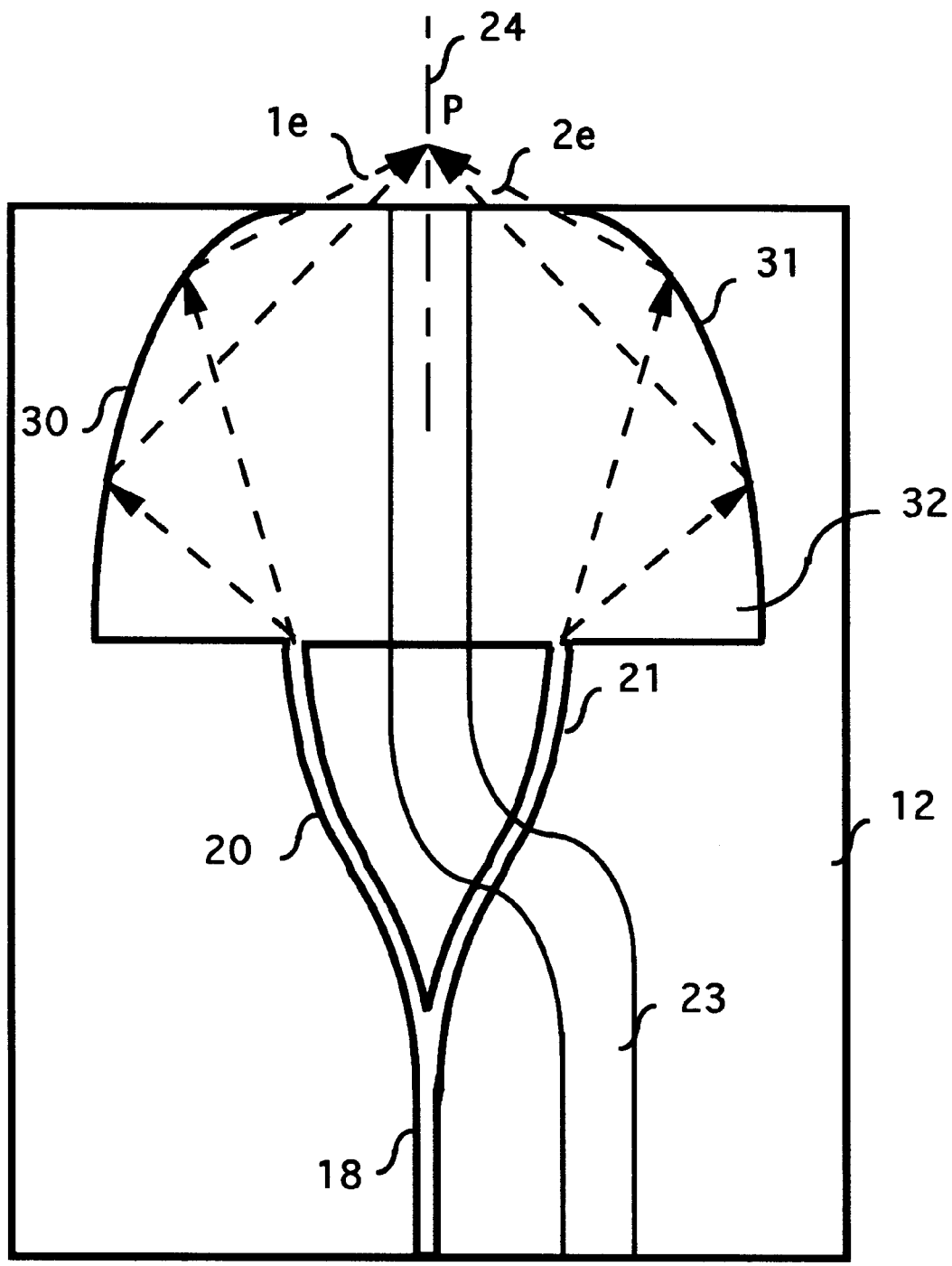

In the particular embodiment represented in FIG. 10, the measuring volume, at the point P, is defined by means of two convergent beams 1e and 2e which cross at the point P. The measuring volume can thus be smaller than when parallel beams are used as in the embodiments described previously. As an example, the measuring volume can have a diameter of about 100 micrometers with parallel beams and can be about 20 to 30 micrometers with convergent beams. Each convergent beam 1e or 2e is formed by a curved mirror respectively 30 or 31 whose focal point is at the point P at the centre of the measuring volume. The light beam output from the guide 20 is reflected by the curved mirror 30 so as to form the convergent beam 1e passing through the point P. Likewise, the light beam output from the guide 21 is reflected by the curved mirror 31 to form the convergent beam 2e also passing through the point P. The intersection of the two beams at the point P forms the interference fringes of the measuring volume.

The curved mirrors 30 and 31 can be achieved very simply by giving a specific shape to the edge of a flat output guide 32 so as to ensure total reflection of the output beams from the guides 20 and 21. When the ion exchange technique with a glass substrate is used, this is achieved very simply by giving the mask a suitable shape in the part designed to form the flat output guide.

The substrate 12 can also be a silicon substrate. The curved mirrors 30 and 31 can then be achieved by engraving the substrate and metallization of the external face of the mirrors.

In FIG. 10, the input emitter guide 18 is placed in the axis of symmetry of the substrate 12, identical to the axis 24 of the input end of the receiver guide 23. The latter could, as in FIG. 8, be straight, arranged in another plane of the substrate 12 than the emitter guides. In FIG. 10 it is situated in the same plane, but its output end is offset to enable connection to the detection circuit 11.

The fibres 13 and 14 (FIG. 4), connected respectively to the input of the emitter guide 18 and to the output of the receiver guide 23, can be connected to the microguides by sticking.

The use of a glass substrate is particularly advantageous since it has a very low intrinsic attenuation, is inexpensive and available in large size, which enables devices of several centimeters in length to be achieved. Moreover, the ion exchange technique for achieving the microguides, with use of a mask, enables easy and very precise reproduction of a predetermined model.

The network of interference fringes is characterized by the spatial separation of the fringes which depends both on the wave length of the input light beam supplied by the laser and on the incline of the axes of the light beams 1 and 2 bounding the measuring volume.

The position of the interference fringes depends on a possible phase difference existing between the two arms of the interferometer formed by the guides 20, 21. In FIGS. 5 to 10, the arms (guides 20, 21) are equal (FIGS. 8 and 10) or appreciably equal (FIGS. 5 to 7) and the fringes are practically centred with respect to the measuring volume. It is possible to provide a phase difference between the two arms, either by fitting two arms of very unequal length or by fitting a phase shifter on one of the arms. In this case the fringes are offset. Current modulation of the laser 3 or a variation of the phase difference then enables the fringes to be made to run in the direction 6 of flow of the fluid (FIG. 4). This can, if necessary, enable the sign of the direction of flow to be detected.

Figure 1:
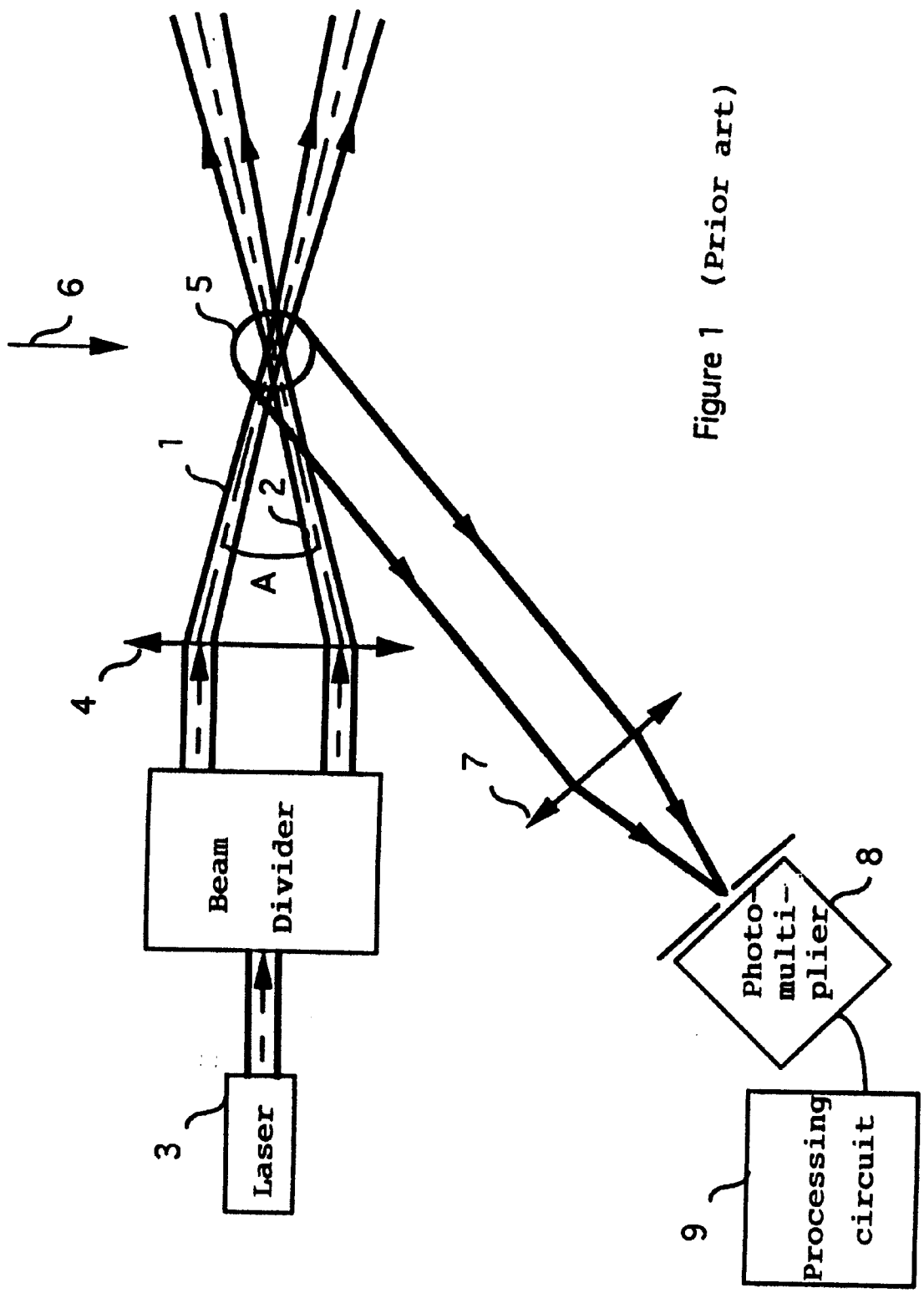
FIG. 1 represents a Doppler effect laser velocimeter according to the prior art.
Figure 2:
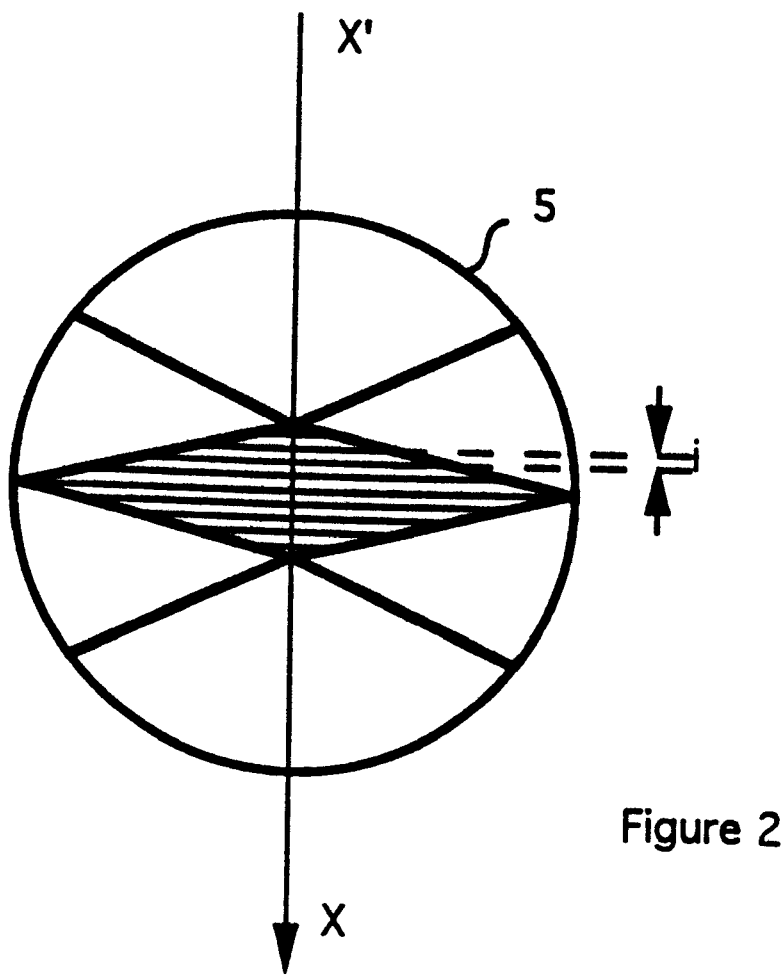
FIG. 2 represents in greater detail the measuring volume of the velocimeter of FIG. 1.
Figure 3:
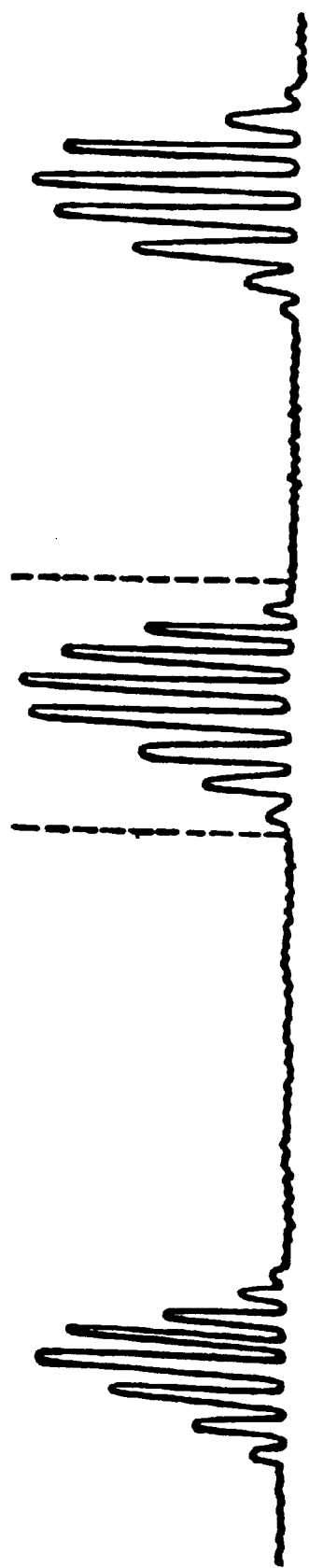
FIG. 3 represents the signals transmitted to the electronic processing circuit of the velocimeter according to FIG. 1.

In the processing circuit 9, measurement of the frequency of the signals inside a sine wave train (FIG. 3) enables a quantity to be obtained representative of the velocity of the particles in movement in the measuring volume 5. The frequency of the sine wave trains can be used for measuring the number of particles. Moreover, the envelope of a sine wave train is representative of the size of the corresponding particle. Processing of the data can be performed in any known manner and will not be explained in greater detail.

The integrated device above enables easy fitting and removal in a wall 16. In addition, the device is both rugged and compact. It does not disturb the fluid flowing along the wall 16 in any way, since the device does not protrude inside the wall. As the light signals do not have to pass through the wall, the device eliminates interference reflections which would be caused thereby and disturbances due to these interference reflections. Furthermore no optic adjustment is necessary, which makes for very ease use in industrial environments.

Such a device is more particularly suitable for determining the velocity, size and number of particles in movement in a liquid. Applications can be envisaged for example in the agribusiness field (e.g. champagne bubbles), in chemistry and biology.

The angle A of the beams 1 and 2, on which the interfringe distance i depends, is preset taking into account the envisaged application and in particular the size of the particles to be examined.

We claim:

1. An optic device for detection of characteristics of particles in movement in a fluid flowing along a wall, a device comprising a light source, means, connected to the light source, for producing at least two mutually coherent light beams forming between them a predetermined angle so as to form an interference zone constituting a measuring volume on the path of the fluid, optic means for detection of the light diffused by particles passing through the measuring volume, optoelectronic means for detection, connected to the optic means for detection and supplying electronic signals representative of the light diffused, and processing means, connected to the optoelectronic means for detection, a device characterized in that the means for producing light beams comprise at least one pair of two emitter optic guides, the optic means for detection comprise at least one optic receiver guide comprising an input end having an axis passing through the centre of the measuring volume, said emitter and receiver guides being achieved on a single substrate by integrated optics techniques, the geometry of the emitter guides being such that the measuring volume is arranged outside the substrate at a preset distance from a face of the substrate, the substrate being mounted in a support designed to be fixed in an orifice of the wall in such a way that said face of the substrate is in contact with the fluid.

2. The device according to claim 1, characterized in that the substrate comprises a flat guide between the emitter optic guides and said face of the substrate.

3. The device according to claim 1, characterized in that the emitter optic guides each comprise, at one end, an adiabatic transition constituted by a broadening of the end of the emitter optic guide so as to form parallel beams.

4. The device according to claim 2, characterized in that the flat guide comprises means for forming convergent beams.

5. The device according to claim 4, characterized in that the means for forming convergent beams comprise curved mirrors having focal points at the centre of the measuring volume.

6. The device according to claim 1, characterized in that the substrate comprises a plurality of pairs of emitter optic guides so as to define a plurality of measuring volumes.

7. The device according to claim 6, characterized in that the measuring volumes are aligned with the axis of the input end of a single receiver guide.

8. The device according to claim 6, characterized in that the measuring volumes are laterally offset, the substrate comprising a plurality of laterally offset associated receiver guides having axes passing respectively through the centre of the associated measuring volume.

9. The device according to claim 1, characterized in that the receiver optic guides are achieved in the substrate in a different plane from the emitter optic guides.

10. The device according to claim 1, characterized in that it comprises means producing a succession of the interference fringes in the interference zone.

* * * * *